United States Patent
Kirenko et al.

(10) Patent No.: US 10,223,890 B2
(45) Date of Patent: Mar. 5, 2019

(54) DETECTING A MOVEMENT AND/OR A POSITION OF AN OBJECT TO BE MONITORED

(71) Applicant: KONINKLIJKE PHILIPS N.V., Eindhoven (NL)

(72) Inventors: Ihor Olehovych Kirenko, Veldhoven (NL); Brian David Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/323,814

(22) PCT Filed: Jul. 2, 2015

(86) PCT No.: PCT/EP2015/065050
§ 371 (c)(1),
(2) Date: Jan. 4, 2017

(87) PCT Pub. No.: WO2016/005255
PCT Pub. Date: Jan. 14, 2016

(65) Prior Publication Data
US 2017/0169691 A1    Jun. 15, 2017

Related U.S. Application Data

(60) Provisional application No. 62/021,237, filed on Jul. 7, 2014, provisional application No. 62/072,705, filed on Oct. 30, 2014.

(30) Foreign Application Priority Data

Dec. 4, 2014   (EP) .................................... 14196182

(51) Int. Cl.
*A61B 5/11* (2006.01)
*G06K 9/00* (2006.01)
(Continued)

(52) U.S. Cl.
CPC ........ *G08B 21/0476* (2013.01); *A61B 5/1115* (2013.01); *A61B 5/1117* (2013.01);
(Continued)

(58) Field of Classification Search
None
See application file for complete search history.

(56) References Cited

U.S. PATENT DOCUMENTS 6,646,556 B1 * 11/2003 Smith ................... A61B 5/1115
340/573.1
9,904,854 B2 * 2/2018 Okada ...................... G06K 9/64
(Continued)

FOREIGN PATENT DOCUMENTS

EP        1837666         1/2008
WO    2013/052123        4/2013

*Primary Examiner* — Matthew C Bella
*Assistant Examiner* — Jose Torres

(57) ABSTRACT

A movement and/or a position of an object (1) to be monitored is detected. At least one marker (2) radiating light is arranged in an area of the object (1) such that a camera (4) can capture images of the marker (2), when the object (1) is in a first position. An image processing unit (6) is enabled to detect the marker (2) in the images and to detect a movement and/or a second position of the object (1) in response to determining that at least a part of the marker (2) cannot be detected in one or more of the images. The object (1) may be a person laying in a bed and the marker (2) may be arranged adjacent to the bed's lying area (3) so that the system can detect when the person leaves the bed and notify nursery staff or an emergency central.

17 Claims, 4 Drawing Sheets

(51) Int. Cl.
*G06K 9/78* (2006.01)
*G06T 7/73* (2017.01)
*G06T 7/246* (2017.01)
*G08B 21/04* (2006.01)

(52) U.S. Cl.
CPC ........ *A61B 5/1127* (2013.01); *G06K 9/00342* (2013.01); *G06K 9/00369* (2013.01); *G06K 9/00771* (2013.01); *G06K 9/78* (2013.01); *G06T 7/248* (2017.01); *G06T 7/74* (2017.01); *G08B 21/0446* (2013.01); *G06T 2207/10048* (2013.01); *G06T 2207/30004* (2013.01); *G06T 2207/30196* (2013.01); *G06T 2207/30204* (2013.01)

(56) References Cited

U.S. PATENT DOCUMENTS

| | | | | |
|---|---|---|---|---|
| 2004/0046668 A1* | 3/2004 | Smith | ................... | A61B 5/1115 340/573.7 |
| 2006/0171560 A1 | 8/2006 | Manus | | |
| 2008/0317281 A1* | 12/2008 | Goldbach | ............ | G06F 19/3412 382/103 |
| 2009/0119843 A1* | 5/2009 | Rodgers | ................ | A61B 5/1115 5/611 |
| 2012/0026308 A1* | 2/2012 | Johnson | ............. | G06K 9/00369 348/77 |
| 2012/0212582 A1* | 8/2012 | Deutsch | ................ | G08B 21/245 348/46 |
| 2014/0104404 A1* | 4/2014 | Locke | .................... | G08B 21/02 348/77 |
| 2014/0267625 A1* | 9/2014 | Clark | .................... | A61B 5/002 348/46 |
| 2014/0267663 A1* | 9/2014 | Yasukawa | ................. | H04N 7/18 348/77 |
| 2014/0325760 A1* | 11/2014 | Murai | .................... | A61G 7/018 5/616 |
| 2014/0363089 A1* | 12/2014 | Uetsuji | ................. | G06T 7/0051 382/199 |
| 2015/0320339 A1* | 11/2015 | Larson | ................. | A61B 5/1113 600/595 |

* cited by examiner

DETECTING A MOVEMENT AND/OR A POSITION OF AN OBJECT TO BE MONITORED

CROSS REFERENCE TO RELATED APPLICATIONS

This application is the U.S. National Phase application under 35 U.S.C. § 371 of International Application No. PCT/EP2015/065050, filed Jul. 2, 2015, published as WO 2016/005255 on Jan. 14, 2016, which claims the benefit of U.S. Provisional Patent Application No. 62/021,237 filed Jul. 7, 2014, and U.S. Provisional Patent Application No. 62/072,705 filed Oct. 20, 2014, and European Patent Application Number 14196182.1 filed Dec. 4, 2014. These applications are hereby incorporated by reference herein.

FIELD OF THE INVENTION

The invention relates to a system, method and computer program for detecting a movement and/or a position of an object to be monitored.

BACKGROUND OF THE INVENTION

The detection of movements and/or a position of an object is particularly important in the health sector. Here, it is particularly important to keep lying patients moving unsafely without assistance safe from harm due to falling out of the bed, and to ensure the correct positioning of means that are sometime used for preventing falling, such as, for example, bed rails. Moreover, it has to be ensured that medical devices attached to a patient, such as, for example, body sensors, respiratory masks and the like, are positioned correctly in order for them to work properly.

To address these issues, patients may be monitored frequently by nursery staff. However, this imposes a huge workload on the nursery staff of a health care facility. Moreover, a sufficiently frequent monitoring can usually not be guaranteed for patients at their home, in particular when they live alone.

Therefore, there is a need for an automated monitoring. Moreover, such an automated monitoring should avoid disturbances of the patients to the largest possible extent.

U.S. 2006/0171560 relates to a system for locating and tracking an object, particularly a patient, using a camera array. In this system, the object is provided with markings, which are recorded via the camera array and which are extracted from the recordings in order to monitor their locations. The system determines the spatial position of the object on the basis of the locations of the markings. Thus, the system particularly allows for an automated monitoring of an object. However, the system tracks all movements of the object resulting in a movement of the markings. Thus, in case the object is a patient, the system may affect the patient's privacy.

SUMMARY OF THE INVENTION

It is an object of the present invention to allow for an automated detection of a movement and/or a position of an object in an unobtrusive way.

In a first aspect of the present invention, a system for detecting a movement and/or a position of an object to be monitored is suggested. The system comprises a camera for capturing images, the camera being sensitive to light in a predetermined wavelength range. Further, the system comprises at least one marker radiating light in the predetermined wavelength range, the marker being located in an area of the object in such a way that the camera can capture images of the marker when the object is in a first position. Moreover, the system comprises an image processing unit enabled to detect the marker in the images, the image processing unit being configured to detect a movement and/or a second position of the object in response to a determination that at least a part of the marker cannot be detected in one or more of the images, the determination being indicative of the movement and/or the second position of the object.

Since a movement and/or the second position of the object is detected on the basis of one or more captured image when at least part of the marker cannot be detected in one or more images, the system allows for an unobtrusive monitoring of the object. Furthermore, the detection relies on the visibility of a marker or a part thereof in the captured images, which can be ascertained easily and reliably.

Moreover, the system does not require a direct recognition of the object and/or its movements in the images. Rather, only the marker needs to be detected in the images and a movement of the object is only detected when it changes the visibility of the marker. Any other movements are "invisible" for the system. This guarantees privacy particularly in case the object is a person.

In this respect, the visibility of the marker or the change of the visibility of the marker is indicative of a movement and/or the position of the object as the marker is arranged in an area of the object in such a way that the camera can capture images of the marker, when the object is in the first position. This does particularly mean that the marker is arranged in the vicinity of the object or attached thereto. And, the marker is arranged such that it is obscured from the camera's view when the object moves and/or is in the second position so that the movement and/or the positioning of the device in the second position results in a detectable absence of the marker in the camera images. Thus, it is particularly to be understood that the system does not directly determine the second position of the object. Rather, the system determines that the object is not in the first position. Hence, the object can, in principle, be in any specific position differing from the first position.

Preferably, the camera is sensitive substantially only in the predetermined wavelength range. For this purpose, the camera may be provided with an optical filter which only light in the predetermined wavelength range can pass. Hereby, the contrast between the marker and any background in the images captured by the camera can be increased. This simplifies the detection of the marker by the image processing unit.

The marker is configured to radiate light in the predetermined wavelength range. This does particularly mean that marker is configured to reflect light or actively emit light. In one embodiment, the marker is configured as a passively radiating device. In this embodiment, the system further comprises a light source emitting light in the predetermined wavelength range and the marker reflects the light emitted by the light source. Such a configuration is usually less costly than the use of actively emitting markers. However, it is likewise possible that the marker is configured to actively emit light in the predetermined wavelength range. In this case, the light source can be dispensed with.

Preferably, the light source or the marker emits light substantially only in the predetermined wavelength range.

In a further embodiment, the predetermined wavelength range is contained in a part of the spectrum invisible to the human eye. Particularly the predetermined wavelength range may be contained in the infrared spectrum. Hereby, the disturbance of persons, which may be the object of the monitoring or which may stay in the vicinity of the object to be monitored, can be reduced, particularly in case the light source or marker does substantially only emit light in the predetermined wavelength range.

One embodiment provides that the marker is located adjacent to the object and that the image processing unit is configured to detect a movement of the object when an interruption of the visibility at least of the part of the marker in a series of captured images is determined. Here, the term interruption relates to a change of the visibility of the marker to an invisible "state" in the series of images. After this change of the visibility, the marker may or may not be visible again in further images captured later. It is one advantage of this embodiment that the object itself does not have to be provided with the marker. This does particularly prevent any inconvenience caused by the marker in case the object to be monitored is a person. Moreover, the system configured in accordance with this embodiment is only responsive to movements of the object obscuring the marker from the camera's view. Other movements of the object are not registered so that any privacy issues are prevented in case the object to be monitored is a person.

In a related embodiment, plural markers are arranged adjacent to each other. In this embodiment, a movement of the object may only be detected when at least a part of each marker cannot be detected in an image. Hereby, the reliability of the movement detection can be increased.

Moreover, the use of a plurality of markers allows for determining a direction of the movement of the object. In this regard, a related embodiment provides that the image processing unit is configured to determine a direction of the movement of the object based on an order in which interruptions of the visibility at least of parts of the markers in the series of captured images are determined.

In addition or as an alternative, the use of a plurality of markers allows for determining the speed of the movement of the object. In this regard, a further related embodiment provides that the image processing unit is configured to determine a speed of a movement of the object based on a difference between a point in time of a determined interruption of the visibility of at least part of first marker in a series of captured images and a point in time of a determined interruption of the visibility of at least part of a second marker in the series of captured images.

The embodiments comprising one or more markers arranged adjacent to the object particularly allow for a detecting a movement of the object to be monitored. In one application, the object may be a person lying in a bed and the one or more markers are arranged in or adjacent to a lying area of the bed.

A movement of the person detected in the system may particularly be indicative of an unintentional bed leave or fall of the person. Therefore, the system can be used to detect such unintentional bed leaves.

Such a bed leave may be detected in case the system detects a movement of the person. When the determined direction of movement and/or the estimated speed of the movement are taken into account, a more reliable detection of unintentional bed leaves is possible. So, it is possible to distinguish movements out of the bed and into the bed on the basis of the determined direction of movement. Moreover, falls may be distinguished from intentional bed leaves on the basis of the estimated speed of the person's movement. Thus, the system may indicate an unintentional bed leave in response to a detection of a movement of the person in a direction out of the bed and/or with an estimated speed above a predetermined threshold value.

In a further embodiment, the marker is attached to the object to be monitored. In this embodiment, the system is particularly capable of detecting whether the object is in one of two or more possible positions.

In accordance with a related embodiment, the object to be monitored can be in the first position or second position, and the marker is attached to the object in such a way that the camera cannot capture images of the marker when the object is in the second position. Thus, the system is capable of detecting the second position of the object in case of an absence of the marker in one or more camera images which is due to the marker being obscured from the camera's view when the object is in the second position.

In this configuration, the object may particularly be a bed rail foldable from a deactivated position into an activated position and the system may be capable of monitoring the positioning of the bed rail, wherein the first position corresponds to the activated position and the second position corresponds to the deactivated position.

Similarly, the system can detect positions of other objects. Such other objects particularly include medical devices attached to the body of a person. These objects are in the aforementioned first position when they are properly attached to the person's body. The aforementioned second position corresponding to the position detectable in the system corresponds to a position in which the object is displaced from its proper position in such a way that the marker is obscured from the camera's view.

In a further embodiment, the system is configured to initiate an alarm routine in response to a detection of a movement and/or the second position of the object to be monitored. In case of the aforementioned specific implementations in which the object is a person, a bed rail or a medical device attached to a person, the alarm routine may include a notification of nursery staff and/or an emergency center which can provide help in case of an alarm.

Furthermore, the system may be configured to detect a badge having a different shape than the marker and radiating light in the predetermined wavelength range in the images and to deactivate the initiation of the alarm routine in response to a detection of the badge in one of the images. Such a badge may be carried by caregivers. Thus, it is possible for the system to detect the presence of a caregiver and to deactivate the initiation of the alarm routine which is not necessary in case a caregiver is present.

In a further aspect of the present invention a method for detecting a movement and/or a position of an object to be monitored is presented, wherein the method comprises:

capturing images using a camera, the camera being sensitive to light in a predetermined wavelength range, wherein at least one marker is arranged in an area of the object in such a way that the camera can capture images of the marker, when the object is in a first position, the marker radiating light in the predetermined wavelength range;

evaluating the images in an image processing unit enabled to detect the marker in the images; and detecting a movement and/or a second position of the object in response to determining that at least a part of the marker cannot be detected in one or more of the images.

In a further aspect of the present invention a computer program is presented, which is executable in an image processing unit of a system according to the invention and its embodiments. The computer program comprises program code means for causing the image processing unit to evaluate the images captured using the camera and to detect a movement and/or the second position of the object in response to determining that at least a part of the marker cannot be detected in one or more of the images, when the computer program is executed in the image processing unit.

It shall be understood that the system of claim 1, the method of claim 14 and the computer program of claim 15 have similar and/or identical embodiments, in particular, as defined in the dependent claims.

It shall be understood that an embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
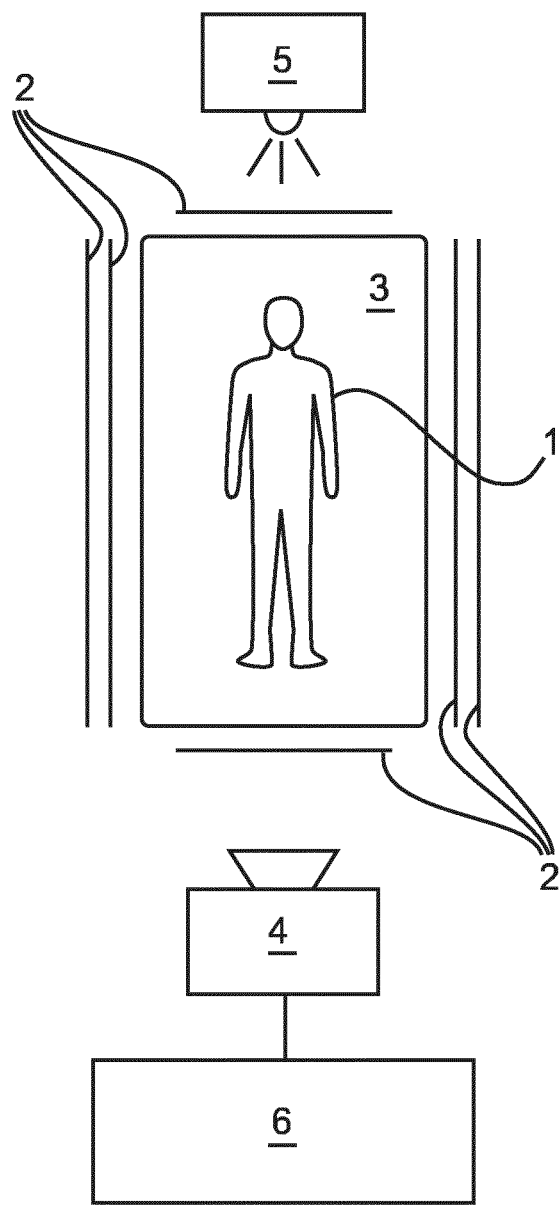
FIG. 1 shows schematically and exemplarily an embodiment of a system for detecting a movement of a person out of a lying area of a bed.

FIG. 1 shows schematically and exemplarily a system for detecting a movement of an object to be monitored. In this exemplary embodiment, the system is operated as a bed occupancy monitor detecting falls of person 1 out of a bed or other unintentional bed leaves of the person 1, which constitutes the object to be monitored in this embodiment. The person 1 may particularly be an elderly, ill or injured person for which an increased risk of unintentional bed leaves or an increased risk to be injured upon such an unintentional bed leave exists.

The system configured in accordance with this embodiment may be operated in a hospital, nursing home or similar health care facility, or it may monitor the person at home. Upon having detected an unintentional bed leave, the system may initiate an alarm routine. This alarm routine may include a notification of nursery staff of the health care facility operating the system, or—particularly when the system is operated at the person's home—the alarm routine may include an automated emergency call to an emergency center.

In the embodiment shown in FIG. 1, the system for detecting a movement of the person 1 comprises markers 2 which are located adjacent to one or more sides of the lying area 3 of the bed of the person 1. The markers 2 may be configured as continuous stripes extending along the associated sides of the lying area 3. However, other patterns, such as, for example, discontinuous stripes are likewise possible.

Preferably, the markers 2 are arranged at all open sides of the lying area 3, i.e. at those sides which are not provided with bed rails or similar means for preventing the person 1 to leave the bed. The open sides usually comprise the longitudinal sides of the lying area 3 so that these sides may be provided with at least one marker 2, respectively. In addition, the transversal sides of the lying area 3 may be provided with at least one marker as shown in FIG. 1, particularly when they are open sides.

In one configuration, exactly one marker 2 is provided at each relevant side of the lying area 3 of the bed. Preferably, this marker 2 does substantially extend along the complete length of the respective side of the lying area 3. By means of this marker 2, the system is capable of detecting bed leaves of the person 1 via the associated edge of the lying area 3.

Optionally, more than one marker 2 may be provided at one or more side as shown in FIG. 1 with respect to the longitudinal sides of the lying area 3. The optional additional markers 2 enable the system to determine the speed of the person's movement out of the bed and/or the direction of movement. Moreover, such additional markers 2 can facilitate a determination in which part of the lying area 3 (e.g. the head or foot region of the lying area 3) the person 1 is crossing the edge of the lying area 3.

For attaching the markers 2 adjacent to their associated edges of the lying area 3, several options exist. For instance, the markers 2 can be attached to the frame of the bed in a region surrounding the lying area 3. This configuration has the advantage, that the markers 2 are fixedly attached relative to the lying area 3. However, the markers 2 can also be attached in any other suitable way. So, they can also be attached to the floor adjacent to the bed, for example.

Moreover, the markers 2 may be attached at their respective positions by means of any suitable fixing means. In one embodiment, the markers 2 may be configured as adhesive strips which are glued on the bed frame or another support. As an alternative, the markers 2 may be formed by a paint applied to the bed frame or another support, or they may be screwed in place, for example.

The markers 2 radiate light which is collected by means of a video camera 4. In one configuration, the markers 2 radiate light substantially only in a predefined wavelength range. This means that the markers 2 radiate less or no light in other wavelength ranges. Preferably, the predefined wavelength range is outside the visible electromagnetic spectrum. In particular, the wavelength range can be in the infrared spectrum. Hence, the light radiated by the markers 2 is not visible for the person 1 and, thus, the radiated light does not disturb the person 1. In particular, this makes it possible to operate the system at night without having to visibly illuminate the room in which the markers 2 are used.

The markers 2 may be configured as passively radiating devices which reflect light emitted by a light source 5. In this case, the markers 2 may have a high reflectivity within the predetermined wavelength range. In other wavelength regions, the markers 2 preferably have a lower reflectivity than in the predetermined wavelength range. In order to achieve this property, the markers 2 may comprise a material which reflects light in the predetermined wavelength range and absorbs light in other wavelength regions. One example of such a material which does only reflect light in a wavelength range in the infrared spectrum is Warrior GloTape, manufactured by Brosi I.D. Systems of New Richmond, Wis.

The light source 5 does preferably only emit light in the predetermined wavelength range. Apart from this property, any suitable light source 5 known to a person skilled in the art can be used. Further, the light source 5 is positioned and aligned in such a way that the markers 2 are directly illuminated by the light emitted by the light source 5. For this purpose, the light source 5 may be positioned—in the vertical direction—at a greater height than the lying area 3 of the bed. In the horizontal plane, the light source 5 may be positioned above the lying area 3 or adjacent thereto, e.g. in the area of one of the transversal sides. In order to mount the light source 5 at such a position, the light source 5 may be attached to a wall located adjacent to the bed, or it may fixedly attached to the bed frame by means of a suitable fixing means connecting the light source 5 and the frame of the bed.

In an alternative embodiment, the markers 2 are configured as actively radiating devices. In this embodiment, the markers 2 themselves are configured as active light sources emitting light in the predetermined wavelength range. The light is preferably emitted along the complete longitudinal extension of the markers 2. Thus, the markers 2 may be configured as actively emitting luminous strips. The light source 5 used for illuminating the passive markers 2 can be dispensed with in this alternative embodiment.

The camera 4 may be configured as a digital video camera continuously capturing series of pictures with a certain image rate. The camera 4 can be an off-the-shelf digital camera, which allows for a low-cost implementation of the system. Preferably, the camera 4 is substantially only sensitive to light within the predetermined wavelength range. This may be achieved by means of a suitable optical filter positioned in front of the camera objective or within the camera optic. This filter is configured in such a way that light within the predetermined wavelength range can pass the filter, while light within other wavelength ranges is blocked by the filter. Such a selective sensitivity of the camera 4 in the predetermined wavelength range does particularly enhance the contrast between the markers and any background in the captured images, because any background light in other wavelength regions is blocked.

Preferably, the camera 4 is positioned and aligned in such a way that captured images contain the markers 2 completely. For this purpose, the camera 4 may be positioned at a greater height than the lying area 3 in the vertical direction. In the horizontal plane, the camera 4 may be positioned above the lying area 3 or adjacent thereto, e.g. at one of the transversal sides. In such a position, the camera 4 can be suitably aligned to capture images including the markers 2 completely. Similar to the light source 5, the camera 4 may be attached to a wall located adjacent to the bed, or it may be fixedly attached to the bed frame by means of a suitable fixing means connecting the camera 4 with the bed frame.

When the system comprises the light source 5, i.e. when markers 2 are configured as passively radiating devices, the light source 5 is preferably positioned in such a way that differences between the incident angles of the light hitting the markers 5 and the emergent angles in the direction towards the camera 4 are as small as possible. Hereby, it can be ensured that a high percentage of the light hitting the markers 2 is reflected in a direction towards the camera 4. In order to achieve such a relative arrangement of the light source 5 and the camera 4, the light source 5 and the camera 4 may, for example, be mounted at opposite transversal sides of the lying area 3 in a approximately the same height and with approximately the same distance to the lying area 3.

Images captured by means of the camera 4 are processed in an image processing unit 6 connected to the camera 4. The image processing unit 6 is adapted to automatically recognize the markers 2 in the images captured by the camera 4. Moreover, the image processing unit 4 is capable of registering obscurations of the markers 2 and to detect bed leave moments on the basis of detected obscurations of one or more markers 2.

The image processing unit 6 may be configured as a computing device, such as a personal computer or the like. For processing the images captured by the camera 4, the image processing unit 6 may particularly comprise a suitable image recognition algorithm. This algorithm may recognize the markers 2 in the images, and it may detect obscurations of the markers 2. The algorithm may be included in a software program executed on the computing device forming the image processing unit 6. In addition, the image processing unit 6 comprises further functionality for performing certain actions to be described herein below in response to the detection of an obscuration of one or more markers 2. This functionality may likewise be provided by a suitable software program.

In one embodiment, the camera 4 is configured in such a way that parts of the camera's sensing area can be deactivated so that the camera 4 does only sense light hitting the remaining active parts of the sensing area. In this embodiment, the camera 4 may be controlled such that only the parts of the sensing area collecting the light radiated by the markers 2 are activated while the remaining parts of the sensing area are deactivated. When the camera 4 is operated in such a way, the images captured by the camera 4 do not comprise the person 1 as long as the person 1 does not cross one of the markers 2. Hereby, the protection of the person's privacy can be further improved.

As said above, the system may comprise exactly one marker at one or more sides of the bed's lying area 3 in one embodiment, which will now be described in more detail.

In this embodiment, the monitoring of the person's movements may be started when the person 1 is lying in the lying area 3. The corresponding initiation of the monitoring may be made manually by an operator of the monitoring system, such as a nurse, after the operator has made sure that the person 1 is positioned in the lying area 3.

During the monitoring process, the image processing unit 6 evaluates the images captured by the camera 4 substantially continuously. This means that each image is evaluated or that the evaluation is made in regular intervals, e.g. for each second, third or fourth image. For each evaluated image, the image processing unit 6 may determine whether the existing markers 2 can be detected and whether these markers 2 are completely shown in the image. This determination may be made on the basis of a comparison of the image with a reference pattern which is expected to be present in the image when all markers 2 are completely shown.

The reference pattern may be automatically or semi-automatically derived from a reference image completely showing the markers before the monitoring of the person's movements is started. In particular, the reference image may be captured upon a corresponding command given by an operator in a situation in which the markers are not covered by the person 1 or any other object. The reference image may then be evaluated by the image processing unit 6 in an automatic or semi-automatic (i.e. operator-assisted) learning process in order to derive the reference pattern from the image. Thereupon, the derived reference pattern may be stored in the image processing unit 6 for carrying out the aforementioned comparisons with camera images during the monitoring of the person's movements.

When the image processing unit 6 determines that one of the markers 2 is at least partly not shown in one evaluated image, it may detect a bed leave moment. This is due to the fact that an obscuration of the marker 2 in the image is likely caused by a movement of the person's body across the marker 2. And, since the person was lying in the lying area 3 before the obscuration occurred, the person is likely to leave the bed during this movement.

In a further configuration, the image processing unit 6 may additionally estimate the size of the obscured part of the relevant marker 2 and may only detect a bed leave moment when the estimates sizes is greater than a predetermined minimum size. Hereby, it can be prevented that obscurations of only small parts of a marker 2, which may occur when the person 1 reaches out with her arm or leg, for example, are erroneously detected as bed leave moments.

In response to the detection of a bed leave moment, the image processing unit 6 may initiate an alarm routine. As said above, this alarm routine may include the notification of nursery staff and/or an emergency center.

In a further embodiment of the monitoring system, more than one marker 2 is provided at least at one side of the lying area 3 of the bed. Preferably, at least the open longitudinal sides of the lying area 3 are provided with more than one marker 2 as the person 1 will leave the bed via such sides in most cases. Using a plurality of markers 2 at a certain side of the lying area 3, the system is capable of determining the direction and/or speed of a person's movement across the markers 2.

On the basis of the information about the direction of a movement, the system can distinguish between movements into the lying area 3 and movement out of the lying area 3. Thus, the system can distinguish between bed leaves and entries into the bed. Therefore, the system does not require a definite "initial state" in which the person is lying in the lying area 3 at the initiation of the monitoring process. Rather, the monitoring by the system can be arbitrarily started irrespective of the position of the person 1.

In the following, the operation of the system in this embodiment is described with respect to the monitoring of movements of the person 1 in a direction of one side of the lying area 3 which is provided with plural markers 2.

During the monitoring process, images captured by the camera 4 are evaluated substantially continuously by the image processing unit 6 as described in connection with the aforementioned embodiment using a single marker 2. The evaluation of each image comprises a determination whether the plural markers 2 at the relevant side of the lying area 3 can be detected and whether these markers 2 are completely shown in the image. The determination may again be made on the basis of a comparison of the pattern corresponding to the markers 2 detected in the image with a reference pattern comprising all markers 2. This reference pattern may be determined in a similar way as in the embodiment described above.

Movements of the person 1 into or out of the lying area 3 are detected on the basis of an evaluation of a series of images in which the markers 2 are obscured one after the other. In such a series of images, the image processing unit 6 determines the order in which the markers are obscured. When it determines that the outermost marker 2 (i.e. the marker having the largest distance to the lying area 3) is obscured at first and the innermost marker (i.e. the marker having the smallest distance to the lying area 3) is the last obscured marker 2, the image processing unit 6 detects a movement of the person 1 into the lying area 3. In this case, no further actions may be initiated. In particular, the image processing unit 6 may not initiate an alarm routine in this case.

If the processing unit 6 determines that the outermost marker 2 is obscured after the innermost marker 2, it detects a bed leave moment. This is due to the fact that the person crosses the markers 2 in a direction from inside the lying area 3 to outside the lying area 3, when the outermost marker 2 is obscured after the innermost marker 2. In response to the detection of the bed leave moment, the image processing unit 6 may initiate an alarm routine as described above.

In addition or as an alternative to the determination of the direction of the person's movement, the image processing unit 6 may estimate the speed of the person's movement in case a bed leave moment is detected. As described herein below this estimation is also made using a plurality of markers 2 arranged at a side of the lying area 3 of the bed via which the person 1 is leaving the bed. Upon the estimation of the speed of movement, the alarm routine may only be initiated, when the estimated speed is greater than a predetermined threshold value. If the estimated speed is below the threshold value, the image processing unit 6 may not initiate the alarm routine.

The threshold value may be selected in such a way that the low speeds below the threshold value correspond to the typical speeds of movement when a person 1 does intentionally leave the bed. Unintentional bed leaves, such as falls, typical involve higher speeds. Thus, it is possible to distinguish between intentional bed leaves and unintentional bed leaves by comparing the estimated speed of movement with the threshold value.

For estimating the speed of movement, the image processing unit 6 may determine a time difference between the points in time at which the detected obscurations of the markers 2 begin, respectively. On the basis of this time difference and the distance between the markers, the image processing unit 6 calculates the estimated speed of movement.

Figure 2A:
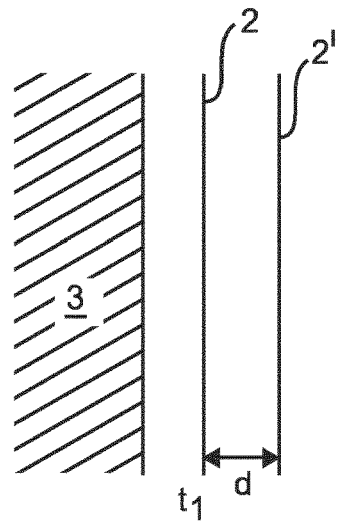
FIG. 2a shows schematically and exemplarily an obscuration of one marker in an image captured in the system at a first point in time.
Figure 2B:
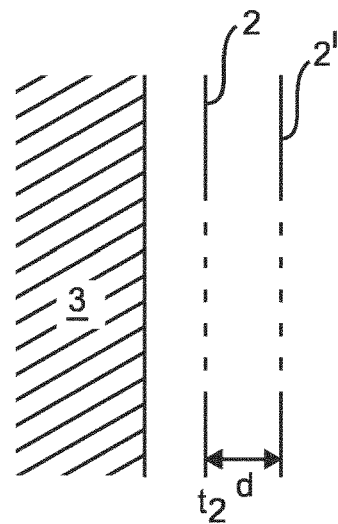
FIG. 2b shows schematically and exemplarily an obscuration of the first marker and a second marker in a further image captured in the system at a second point in time.

Schematically, this is a further illustrated in the FIGS. 2a and 2b. Both figures schematically show an excerpt of an image captured by the camera 4 containing a part of the lying area 3 and two markers 2 and 2' associated with one side of the lying area 3 via which the person is leaving the bed. As shown in FIG. 2a, the image processing unit 6 may detect in an image captured at the time $t_1$ an obscuration of the inner marker 2 (obscured parts of the markers 2 and 2' are shown as dashed lines in FIGS. 2a and 2b). Thereupon, the image processing unit 6 also detects an obscuration of the marker 2' in the image captured at the time $t_2$. The distance d between the marker 2 and the marker 2' may be stored as a parameter in the image processing unit 6. On the basis of the times $t_1$ and $t_2$ and the distance d, the image processing unit 6 may calculate an estimated speed v of the person's movement using the relation $v=(t_2-t_1)/d$.

In a further embodiment, the image processing unit 6 determines, in case of a detected bed leave moment, in which region the person is leaving the lying area 3 at first in order to distinguish between intentional bed leaves and falls. In particular, the image processing unit 6 may determine whether the person firstly leaves the lying area 3 in a head region of the lying area 3 or in a foot region of the lying area 3. An unintentional bed leave may only be detected, when the person firstly leaves the lying area 3 in the head region or when the person simultaneously leaves the lying area 3 in the head and foot region. However, the image processing unit 6 may not detect an unintentional bed leave or fall, in case it is determined that the person firstly leaves the lying area 3 in the foot region. This is due to the fact that persons usually start with moving their feet out of the bed, when they intentionally wish to leave the lying area 3 of the bed.

The determination in which part the person firstly leaves the lying area 3 may be made in addition or as an alternative to the estimation of the speed of the person's movement. Particularly, it is in principle also possible to make the determination of the part in which the person firstly leaves the lying area 3 in the embodiment using only a single marker 2 at a particular side of the lying area 3 to detect bed leave moments.

In order to be able to identify the region of the lying area 3 which the person leaves at first, the processing unit 6 uses information about the relative orientation of the lying area 3 with respect to the camera 4. On the basis of this information, the image processing unit 1 associates detected obscuration of the markers 2 to the head or foot region of the lying area 3.

The information about the relative orientation of the lying area 3 with respect to the camera 4 may be pre-stored in the image processing unit 6. In particular, this information may be pre-stored in the image processing unit 6, if there is a fixed relative orientation between the lying area 3 and the camera 4. This may particularly be the case, when the camera is fixedly attached to a bed. In a further configuration, an operator of the system may enter the information about the relative orientation between the lying area 3 and the camera 4, when initiating the monitoring of the person by the monitoring system.

Figure 3:
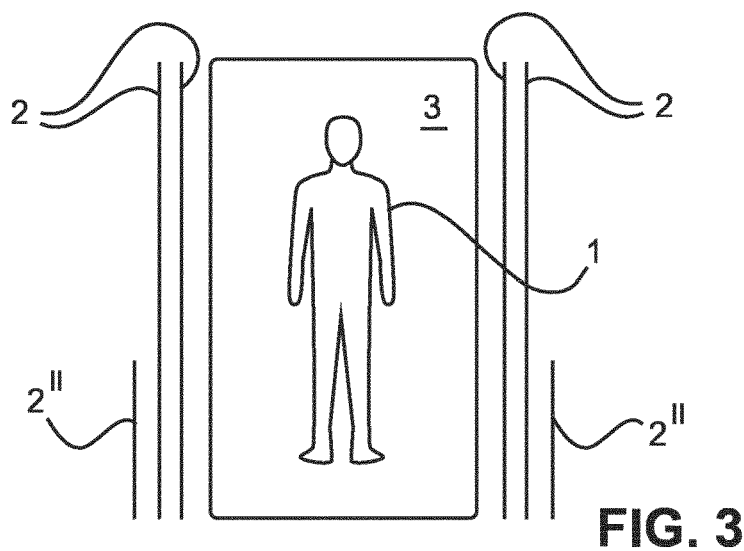
FIG. 3 shows schematically and exemplarily an arrangement of markers relative to a lying area of a bed in one configuration.

Moreover, the image processing unit 6 is capable of automatically detecting the relative orientation between the lying area 3 and the camera 4 in one configuration of the system. In this configuration, markers 2 may be arranged in differing patterns in the head region and foot region of the lying area 3. In particular, there may be at least one marker 2″ which may only be present in the foot or head region of the lying area 3. As shown in FIG. 3, the markers 2″ assisting in the determination of the orientation of the lying area 3 may be provided in addition of one or more further markers 2 arranged at the same edges of the lying area 3. By way of example, FIG. 3 shows such markers 2″ which are only present in the foot region at the longitudinal sides of the lying area 3. When evaluating the images captured by the camera 4, the image processing unit 6 can detect the shortened markers 2″, and can associate the region where such markers 2″ are located with the head or foot region of the lying area 3 depending on where markers 2″ are located.

Figure 4:
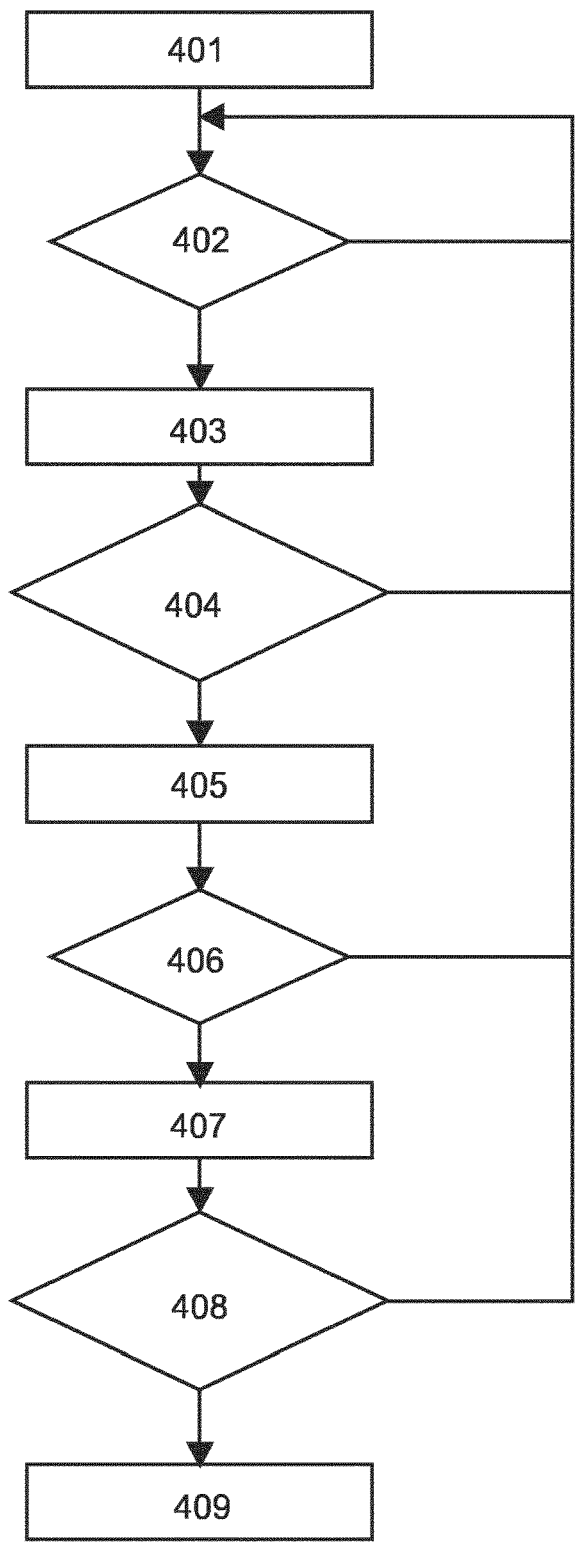
FIG. 4 shows a flowchart schematically and exemplarily illustrating steps of one embodiment of a method for detecting an unintentional bed leave of a person.

FIG. 4 schematically illustrates steps of a method for detecting an unintentional bed leave in the embodiments of the system described above.

In step 401, an image is captured by the camera 4 and passed to the image processing unit 6. Thereupon, the image is evaluated in the image processing unit 6. During this evaluation, the image processing unit determines in step 402 whether at least one marker is completely or partly not present in the image, i.e. whether at least one marker 2 is completely or partly obscured. If this is not the case, no unintentional bed leave is detected and the image processing unit 6 may proceed with the evaluation of the next image captured by the camera 4. If the image processing unit 6 determines in step 402 that at least part of one marker 2 is obscured in the image, it may detect an unintentional bed leave. As described above, this may particularly be the case when only one marker is present.

Optionally, the image processing unit 6 may not make a judgment about the occurrence of an unintentional bed leave at this stage. Rather, the image processing unit 6 may proceed with a determination the direction of the person's movement in step 403 in a way described above. Then, the image processing unit 6 judges whether the person 1 enters or leaves the lying area 3 in step 404. If it is judged that the person is entering the lying area 3, no further action may be made, and the next camera image may be evaluated.

If it is judged in step 404 that the person moves out of the lying area 3, the image processing unit 6 may further estimate the speed v of the person's movement in step 405 in a manner described above. Then, it may compare the estimated speed v with the predetermined threshold $v_{th}$ in step 406. If the estimated speed v is below the threshold $v_{th}$, no unintentional bed leave may be detected and the next image may be evaluated.

If the estimated speed v is larger than the predetermined threshold, the image processing unit 6 may proceed with a determination in which region the person 1 leaves the lying area 3 at first in step 407. In particular, the image processing unit 6 may determine whether the person firstly leaves the lying area 3 in the head or foot region. If it is determined that the person is leaving the lying area 3 in the foot region at first, no unintentional bed leave or fall may be detected, and the image processing unit 6 may proceed with the evaluation of the next image. Otherwise, i.e. if it is determined that the person leaves the lying area 3 in the head region at first or simultaneously leaves the lying area 3 in the head and foot region, the image processing unit may detect an unintentional bed leave or fall in step 409 and may initiate the alarm routine.

It is to be understood that the determination of the direction of the person's movement in step 403, the estimation of the speed of the person's movement in step 405 and the determination in which part the person leaves the lying area 3 at first in step 407 are optional steps of the method. As already explained above, one or more of these steps can also be dispensed with in embodiments of the method. Moreover, the invention is not limited to the order of these steps shown in FIG. 4. Rather, the aforementioned steps, if provided, may be made in any order.

As already explained above, the monitoring system may initiate an alarm routine in case it detects an unintentional bed leave of the person 1. In one embodiment, the system is further configured to detect the presence of a caregiver 7 in the vicinity of the person 1 or the laying area 3. And, if a caregiver's presence is detected, the initiation of the alarm routine may be deactivated. In that regard, the system may evaluate the captured camera images in view of an unintentional bed leave that may only block the initiation of the alarm routine in case an unintentional bed leave is detected. However, it may likewise be provided that the system does also not perform this evaluation during the presence of the caregiver 7.

Figure 5:
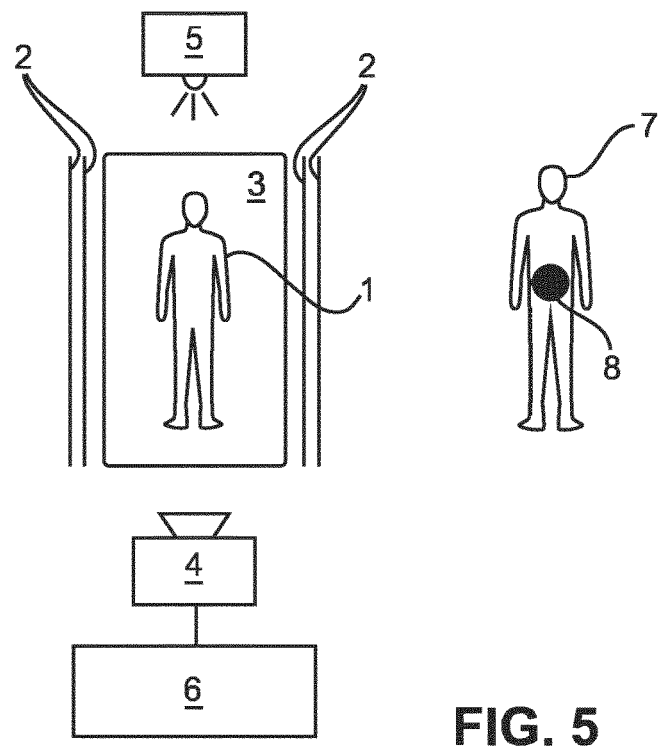
FIG. 5 shows schematically and exemplarily an embodiment of a system capable of detecting the presence of a caregiver in the vicinity of a monitored person.

The presence of the caregiver 7 may particularly be detected on the basis of the images captured by the camera 4. For this purpose, caregivers 7 may be provided with badges 8 which they may attach to their body in such a way that the badges 8 are visible for the camera, when the caregivers 7 are within the camera's view as shown in FIG. 5.

Similar to the markers 2, the badges 8 may radiate light within the predetermined wavelength range in which the camera 4 is sensitive. As the markers 2, the badges 7 may be configured as passively radiating devices reflecting the light emitted by the light source 5, or they may be actively radiating devices emitting light in the predetermined wavelength range. Moreover, the badges 8 have a different shape than the markers 2. For instance, the badges 8 may have a circular shape when the markers 2 are configured as stripes. On the basis of their shape, the image processing unit 6 may distinguish the badges 8 from the markers 2 in the images captured by the camera 4.

In order to determine whether a caregiver 7 is present, the image processing unit 6 checks during the evaluation of the camera images whether these images include a badge 8. In order to be able to detect the badges 8 in the camera images, the image processing unit 6 disposes of information about the shape of the badges 8, which may be presorted in the image processing unit 6. On the basis of this information, the image processing unit 6 may determine whether a pattern having the shape of the badges 8 is present in the images. In case the image processing unit 6 detects the presence of a badge 8 in one or more images in such a way, it may disable the alarm routine as described above.

While in the embodiments described above, a movement of a person 1 across an edge of a lying area 3 of a bed is detected, the system may likewise be configured to detect other movements of person positioned on a laying area 3 of a bed in further embodiments.

In particular, markers 2 may be arranged on the lying area 3 of a bed in a suitable pattern in order to detect movements of a person within the laying area in case an interruption of the presence of at least part of one or more markers 2 is detected. In one example of such a configuration, the markers 2 may be arranged on the lying area 3 of a baby's bed. Here, the markers 2 may be distributed across the complete lying area 3 in predefined distances. In particular, the markers 2 may be distributed across the lying area 3 in regular distances. In this example, the system may be used to monitor motions of the baby by means of a remote terminal device, such as a baby phone, which may be held by the baby's parents or another operator. For this purpose, the image processing unit 6 may transmit a corresponding notification to the terminal device each time it detects an interruption of the presence of at least part of one of the markers 2. Moreover, the image processing unit 6 may determine on the basis of the captured images at which position of the laying area 3 the obscuration of a marker 2 occurred and may include information about this position into the notification. Thus, it is possible to monitor the baby's motions from a remote location.

As an alternative to the use of several markers 2 arranged on the lying area 3, it is also possible to provide the laying area 3 with a surface which does completely radiate light in the predetermined wavelength range. Here, the light radiating surface corresponds to one marker 2, and a motion of the baby is detected when the area of the lying area 3 obscured by the baby lying thereon changes (i.e. when the visibility of a certain part of the surface corresponding to the marker 2 is interrupted). Thus, the image processing unit 6 analyzes the consistency of the of the spatial area of the light radiating surface visible in the images captured by the camera 4, and detects a movement of the baby when it determines that this spatial area changes.

Further embodiments of the monitoring system differ from the aforementioned embodiments in that the position(s) of one or more object is monitored instead of the movement of an object.

Figure 6:
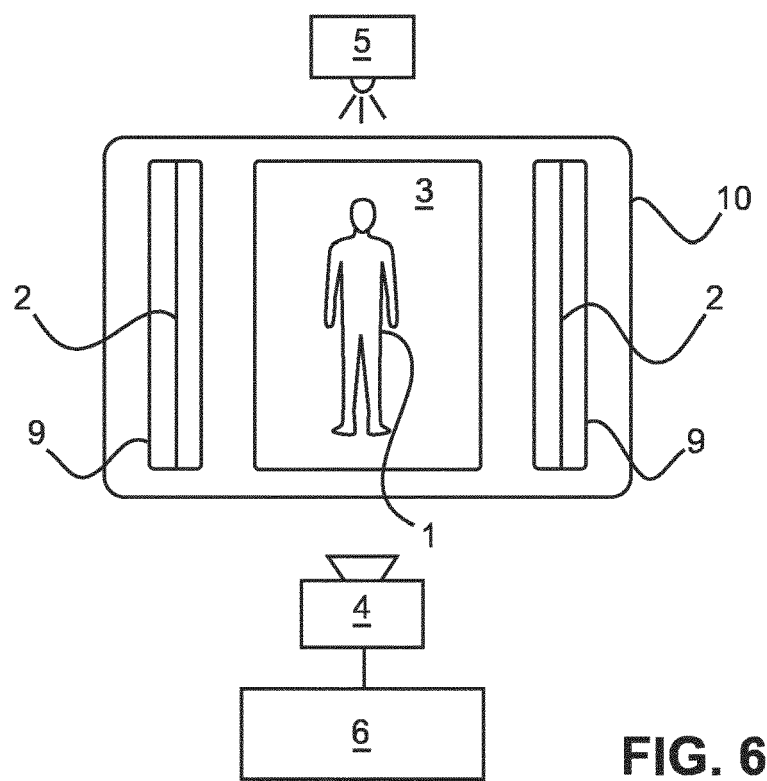
FIG. 6 shows schematically and exemplarily an embodiment of a system for detecting deactivated positions of one or more bed rails.

In the embodiment schematically illustrated in FIG. 6, the objects, the positions of which monitored, are bed rails 9 which are foldable from a deactivated position into an activated upright position in which they prevent a person lying in the bed 10 from falling out of the bed 10. When a person 1 has an increased risk of falling out of the bed 10, the bed rails 9 have to be folded into the activated position. In hospitals and other healthcare facilities, this is typically done by nurses. If the bed rails 9 are not brought into their activated position—e.g., if it was forgotten to fold the bed rails 9 into the activated position—the person 1 is at serious risk to get injured. Therefore, the monitoring system is used in this embodiment to detect situations in which the bed rails 9 are not in their activated position.

For this purpose, the system is configured in an analogue way as in the embodiments described above in connection with a monitoring of movements. However, the markers 2 are attached to the bed rails 9 in such a way that they are only contained in the images taken by the camera 4, when the bed rails 9 are in the activated position as shown in FIG. 6. Thus, when the camera 4 is positioned at a greater height than the upper edge of the activated bed rails 9, the markers 2 may be attached to these upper edges of the bed rails 9. Other than that, the markers 2 can be configured in the same way as in the embodiments of the system described above in connection with the detection of movements of a person 1. Also, the camera 4 can be configured in the same way as in these embodiments. Moreover, the image processing unit 6 connected to the camera 4 can be configured in an analogue way as described above.

In order to detect a situation in which the bed rails 9 are not folded into the activated position, the image processing unit 6 continuously evaluates the images captured by means of the camera 4. During this evaluation, the image processing unit 6 determines whether or not the markers 2 attached to bed rails 9 are present in the camera images. This determination can be made on the basis of a comparison of the camera images with a pattern that is expected when the bed rails 9 are in the activated position. If the image processing unit 6 cannot detect the presence of at least one bed rail 9 in one of the evaluated images, it judges that this bed rail 9 is not in the activated position.

In case such a judgment is made, the image processing unit 6 may again initiate an alarm routine. This alarm routine may again comprise the notification of nursery staff and/or an emergency center. Also in this embodiment, the alarm routine may be disabled in case the system detects the presence of a caregiver 7 in the vicinity of the bed 10 in the way already described above.

Similarly to the monitoring of the positions of the bed rails 9, the system can monitor the position of other objects in further embodiments. Examples of such other objects particularly include medical devices attached to the body of a person, such as, for example, body sensors, respiration masks and the like. Such a medical device may be provided with a marker 2, which may be attached to the medical device in such a way that it is in the camera's view when the medical device is properly attached to the person's body. Then, the system may detect a displacement of the medical device in case the marker 2 can no longer be detected in the camera images. In this case, the system may again initiate an alarm routine.

While the aforementioned embodiments particularly relate to the monitoring of a movement of a person 1 lying in a bed and to the monitoring of objects in the vicinity of a person lying a bed, the invention is not so limited. Rather, the invention can be used to monitor a person 1 in any other position, e.g. sitting on a chair, standing etc. Furthermore, the invention is not limited to an application in the health sector and/or the monitoring of persons. Rather, the system according to invention can also be used to monitor other objects than those mentioned above in a similar manner.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for detecting a movement and/or a position of an object to be monitored, wherein the system comprises:
    a camera for capturing images, the camera being sensitive to light in a predetermined wavelength range;
    at least one elongated marker radiating light in the predetermined wavelength range, the marker being disposed adjacent the object in such a way that the camera can capture images of a portion of the marker, when the object is in a first position,
    an image processing unit enabled to detect changes in the portion of the marker imaged by the camera in the images, the image processing unit being configured to detect a movement and/or a second position of the object in response to a determination that the portion of the elongated marker imaged by the camera in the captured images has changed, the determination being indicative of the movement and/or the second position of the object.

2. The system as defined in claim 1, wherein the predetermined wavelength range is contained in a part of the spectrum invisible to the human eye.

3. The system as defined in claim 2, further including:
    a light source emitting light in the predetermined wavelength range and wherein the elongated marker reflects the light emitted by the light source.

4. The system as defined in claim 1, wherein the at least one elongated marker includes plural markers arranged in a line adjacent to each other such that a number of the plural markers visible to the camera changes with patient movement.

5. The system as defined in claim 4, wherein the image processing unit is configured to determine a direction of the movement of the object based on an order in the markers of the plurality of markers become or cease to be visible to the camera in the series of captured images.

6. The system as defined in claim 4, wherein the image processing unit is configured to determine a speed of the movement of the object based on a difference between a degree of interruption of the visibility of the plurality of markers in the series of captured images at a first point in time and a degree of interruptions of the visibility of a second of the plurality of markers in the series of captured images at a second point in time.

7. The system as defined in claim 1, wherein the object to be monitored is a person lying in a bed and wherein the marker is arranged adjacent to a lying area of the bed.

8. The system as defined in claim 1, wherein the object to be monitored is a bed rail foldable from a deactivated position into an activated position and wherein the first position corresponds to the activated position and the second position corresponds to the deactivated position.

9. The system as defined in claim 1, wherein the imaging processing unit is configured to initiate an alarm routine in response to a detection of a movement and/or the second position of the object to be monitored.

10. The system as defined in claim 1, wherein the system is configured to detect a badge having a different shape than the marker and radiating light in the predetermined wavelength range in the images and to deactivate the initiation of an alarm routine in response to a detection of the badge in one of the images.

11. A method for detecting a movement and/or a position of a monitored patient while preserving privacy of the monitored patient, wherein the method comprises:
    capturing images using a camera, the camera being sensitive to light in a predetermined wavelength range in a part of a spectrum invisible to a human eye, wherein at least one stationary elongated marker is arranged adjacent a patient in such a way that the camera captures images of the marker without imaging the patient to preserve the patient's privacy, when the patient is in a first position, the marker radiating light in the predetermined wavelength range;
    evaluating the images in an image processing unit enabled to detect the marker in the images to determine when a portion of the at least one elongated marker is obscured; and
    detecting a movement and/or a second position of the patient by determining a size and/or a location along the at least one stationary elongated marker of the obscured portion.

12. A non-transitory computer-readable medium carrying software for controlling an image processing unit to perform the method as defined in claim 11.

13. A system for detecting a movement and/or position of a patient on a laying area of a bed, the system comprising:
    at least one elongated marker disposed adjacent the laying area, the marker being configured to reflect light in a predetermined wavelength range contained in a part of a spectrum invisible to the human eye;
    a camera configured to image light in the predetermined wavelength range and generate images of the at least one elongated marker;
    an image processor configured to detect the at least one marker in the image and determine when a portion of the at least one elongated marker is obscured and based on a length of the at least one elongated marker which is obscured, determine whether the patient has entered or left the laying area.

14. The system as defined in claim 13, wherein the at least one elongated marker includes at least two elongated markers disposed in parallel a predetermined distance apart adjacent one side of the laying area; and
    wherein the image processor is further configured to:
    when adjacent portions of the at least two elongated markers are obscured, and based on an order in which the at least two elongated markers become obscured, determine when the patient enters the laying area and when the patient leaves the laying area.

15. The system as defined in claim 14, wherein the image processor is further configured to determine a time between the portions of the two elongated markers being obscured and based on the time, determine a speed with which the patient left the laying area and based on the speed, determine whether the patient fell.

16. The system as defined in claim 13, wherein the image processor is further configured to determine whether the obscured portion of the at least one elongated marker is a portion adjacent the patient's head, a portion adjacent the patient's foot, or an elongated portion adjacent both the patient's head and foot, and in response to the obscured portion being adjacent the head or being the elongated portion extending between the head and the foot, determining that the patient fell out of the laying area.

17. The system as defined in claim 13, further including:
a filter mounted to the camera configured to pass light in the predetermined wavelength range and block light in the visible range such that the images generated by the camera depict the at least one elongated marker and not the patient to preserve patient privacy.

\* \* \* \* \*